United States Patent
Mortier et al.

(10) Patent No.: US 8,439,817 B2
(45) Date of Patent: May 14, 2013

(54) CHORDAE CAPTURING METHODS FOR STRESS REDUCTION

(75) Inventors: Todd J. Mortier, Minneapolis, MN (US); Cyril J. Schweich, Jr., St. Paul, MN (US); Robert M. Vidlund, Maplewood, MN (US)

(73) Assignee: Edwards Lifesciences, LLC, Irvine, CA (US)

( * ) Notice: Subject to any disclaimer, the term of this patent is extended or adjusted under 35 U.S.C. 154(b) by 1857 days.

(21) Appl. No.: 11/060,380

(22) Filed: Feb. 17, 2005

(65) Prior Publication Data
US 2005/0143620 A1 Jun. 30, 2005

Related U.S. Application Data

(60) Continuation of application No. 10/138,520, filed on May 6, 2002, now Pat. No. 6,908,424, which is a continuation of application No. 09/843,078, filed on Apr. 27, 2001, now Pat. No. 6,402,680, which is a division of application No. 09/522,068, filed on Mar. 9, 2000, now Pat. No. 6,264,602, which is a continuation of application No. 09/124,321, filed on Jul. 29, 1998, now Pat. No. 6,077,214.

(51) Int. Cl.
*A61N 1/362* (2006.01)
(52) U.S. Cl.
USPC .............................. 600/16; 600/37; 623/2.1
(58) Field of Classification Search ............. 600/16, 600/37; 623/2.1, 2.12
See application file for complete search history.

(56) References Cited

U.S. PATENT DOCUMENTS

| | | | |
|---|---|---|---|
| 4,192,293 | A | 3/1980 | Asrican |
| 4,261,342 | A | 4/1981 | Aranguren Duo |
| 4,372,293 | A | 2/1983 | Vijil-Rosales |
| 4,409,974 | A | 10/1983 | Freedland |
| 4,536,893 | A | 8/1985 | Parravicini |
| 4,690,134 | A | 9/1987 | Snyders |
| 4,705,040 | A | 11/1987 | Mueller et al. |

(Continued)

FOREIGN PATENT DOCUMENTS

| | | |
|---|---|---|
| DE | 3614292 | 11/1987 |
| DE | 4234127 | 5/1994 |

(Continued)

OTHER PUBLICATIONS

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

(Continued)

*Primary Examiner* — Niketa Patel
*Assistant Examiner* — Alyssa M Alter
(74) *Attorney, Agent, or Firm* — AnneMarie Kaiser; Guy Cumberbatch

(57) ABSTRACT

The device and method for reducing heart wall stress. The device can be one which reduces wall stress throughout the cardiac cycle or only a portion of the cardiac cycle. The device can be configured to begin to engage, to reduce wall stress during diastolic filling, or begin to engage to reduce wall stress during systolic contraction. Furthermore, the device can be configured to include at least two elements, one of which engages full cycle and the other which engages only during a portion of the cardiac cycle.

17 Claims, 11 Drawing Sheets

U.S. PATENT DOCUMENTS

| | | |
|---|---|---|
| 4,936,857 A | 6/1990 | Kulik |
| 4,944,753 A | 7/1990 | Burgess et al. |
| 4,960,424 A | 10/1990 | Grooters |
| 4,997,431 A | 3/1991 | Isner et al. |
| 5,106,386 A | 4/1992 | Isner et al. |
| 5,131,905 A | 7/1992 | Grooters |
| RE34,021 E | 8/1992 | Mueller et al. |
| 5,169,381 A | 12/1992 | Snyders |
| 5,192,314 A | 3/1993 | Daskalakis |
| 5,250,049 A | 10/1993 | Michael |
| 5,284,488 A | 2/1994 | Sideris |
| 5,385,528 A | 1/1995 | Wilk |
| 5,389,006 A | 2/1995 | Noschese |
| 5,433,727 A | 7/1995 | Sideris |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup, III |
| 5,662,704 A * | 9/1997 | Gross ............................ 623/2.1 |
| 5,665,092 A | 9/1997 | Mangiardi et al. |
| 5,682,906 A | 11/1997 | Sterman et al. |
| 5,702,343 A | 12/1997 | Alferness |
| 5,718,725 A | 2/1998 | Sterman et al. |
| 5,733,331 A | 3/1998 | Peredo |
| 5,755,783 A | 5/1998 | Stobie et al. |
| 5,758,663 A | 6/1998 | Wilk et al. |
| 5,800,334 A | 9/1998 | Wilk |
| 5,800,528 A | 9/1998 | Lederman et al. |
| 5,800,531 A | 9/1998 | Cosgrove et al. |
| 5,807,384 A | 9/1998 | Mueller |
| 5,814,097 A | 9/1998 | Sterman et al. |
| 5,840,059 A | 11/1998 | March et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A | 10/1999 | Schweich, Jr. et al. |
| 5,961,549 A | 10/1999 | Nguyen et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,984,857 A | 11/1999 | Buck et al. |
| 5,999,678 A | 12/1999 | Murphy-Chutonan et al. |
| 6,001,126 A | 12/1999 | Nguyen-Thien-Nhon |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,102,944 A | 8/2000 | Huynh et al. |
| 6,110,100 A | 8/2000 | Talpade |
| 6,117,159 A | 9/2000 | Huebsch et al. |
| 6,120,520 A | 9/2000 | Saadat et al. |
| 6,123,662 A | 9/2000 | Alferness et al. |
| 6,125,852 A | 10/2000 | Stevens et al. |
| 6,126,590 A | 10/2000 | Alferness |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,182,664 B1 | 2/2001 | Cosgrove |
| 6,190,408 B1 | 2/2001 | Melvin |
| 6,193,648 B1 | 2/2001 | Krueger |
| 6,197,053 B1 | 3/2001 | Cosgrove et al. |
| 6,206,004 B1 | 3/2001 | Schmidt et al. |
| 6,206,820 B1 | 3/2001 | Kazi et al. |
| 6,217,610 B1 | 4/2001 | Carpentier et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,105 B1 | 6/2001 | Nguyen et al. |
| 6,250,308 B1 | 6/2001 | Cox |
| 6,258,021 B1 | 7/2001 | Wilk |
| 6,260,820 B1 | 7/2001 | Chowdhury |
| 6,269,819 B1 | 8/2001 | Oz et al. |
| 6,283,993 B1 | 9/2001 | Cosgrove et al. |
| 6,309,370 B1 | 10/2001 | Haim et al. |
| 6,314,322 B1 | 11/2001 | Rosenberg |
| 6,332,864 B1 | 12/2001 | Schweich, Jr. et al. |
| 6,332,893 B1 | 12/2001 | Mortier et al. |
| 6,375,608 B1 | 4/2002 | Alferness |
| 6,402,680 B2 | 6/2002 | Mortier et al. |
| 6,406,420 B1 | 6/2002 | McCarthy et al. |
| 6,409,760 B1 | 6/2002 | Melvin |
| 6,443,949 B2 | 9/2002 | Altman |
| 6,532,059 B2 | 3/2003 | Shirai et al. |
| 6,544,180 B1 | 4/2003 | Doten et al. |
| 6,547,821 B1 | 4/2003 | Taylor et al. |
| 6,645,139 B2 | 11/2003 | Haindl et al. |
| 6,651,671 B1 | 11/2003 | Donlon et al. |
| 6,685,646 B2 | 2/2004 | Cespedes et al. |
| 6,695,866 B1 | 2/2004 | Kuehn et al. |
| 6,723,038 B1 | 4/2004 | Schroeder et al. |
| 6,755,777 B2 | 6/2004 | Schweich, Jr. et al. |
| 6,793,618 B2 | 9/2004 | Schweich, Jr. et al. |
| 6,797,002 B2 | 9/2004 | Spence et al. |
| 6,808,488 B2 | 10/2004 | Mortier et al. |
| 7,297,150 B2 | 11/2007 | Cartledge et al. |
| 7,404,824 B1 | 7/2008 | Webler et al. |
| 7,455,690 B2 | 11/2008 | Cartledge et al. |
| 2001/0003986 A1 | 6/2001 | Cosgrove |
| 2001/0029314 A1 | 10/2001 | Alferness et al. |
| 2002/0007216 A1 | 1/2002 | Melvin |
| 2002/0022880 A1 | 2/2002 | Melvin |
| 2002/0026092 A1 | 2/2002 | Buckberg et al. |
| 2002/0029080 A1 | 3/2002 | Mortier et al. |
| 2002/0029783 A1 | 3/2002 | Stevens et al. |
| 2002/0058855 A1 | 5/2002 | Schweich, Jr. et al. |
| 2002/0169360 A1 | 11/2002 | Taylor et al. |
| 2003/0105519 A1 | 6/2003 | Fasol et al. |
| 2003/0191538 A1 | 10/2003 | Buckberg et al. |
| 2004/0002719 A1 | 1/2004 | Oz et al. |
| 2004/0024286 A1 | 2/2004 | Melvin |
| 2004/0059181 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0102678 A1 | 5/2004 | Haindl |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |

| | | | |
|---|---|---|---|
| 2006/0052868 | A1 | 3/2006 | Mortier et al. |
| 2010/0023117 | A1 | 1/2010 | Yoganathan et al. |
| 2010/0063586 | A1 | 3/2010 | Hasenkam et al. |

FOREIGN PATENT DOCUMENTS

| | | |
|---|---|---|
| DE | 29619294 | 8/1997 |
| DE | 19947885 | 4/2000 |
| EP | 0583012 | 2/1994 |
| EP | 0820729 | 1/1998 |
| EP | 1943982 | 7/2008 |
| EP | 2298237 | 3/2011 |
| WO | 9119465 | 12/1991 |
| WO | 9506447 | 3/1995 |
| WO | 9516407 | 6/1995 |
| WO | 9516476 | 6/1995 |
| WO | 9604852 | 2/1996 |
| WO | 9640356 | 12/1996 |
| WO | 9724082 | 7/1997 |
| WO | 9724083 | 7/1997 |
| WO | 9724101 | 7/1997 |
| WO | 9803212 | 1/1998 |
| WO | 9814136 | 4/1998 |
| WO | 9817347 | 4/1998 |
| WO | 9818393 | 5/1998 |
| WO | 9826738 | 6/1998 |
| WO | 9829041 | 7/1998 |
| WO | 9832382 | 7/1998 |
| WO | 9911201 | 3/1999 |
| WO | 9913777 | 3/1999 |
| WO | 9930647 | 6/1999 |
| WO | 9944534 | 9/1999 |
| WO | 9944680 | 9/1999 |
| WO | 9952470 | 10/1999 |
| WO | 9956655 | 11/1999 |
| WO | 0002500 | 1/2000 |
| WO | 0003756 | 1/2000 |
| WO | 0006026 | 2/2000 |
| WO | 0006028 | 2/2000 |
| WO | 0013722 | 3/2000 |
| WO | 0018320 | 4/2000 |
| WO | 0027304 | 5/2000 |
| WO | 0028912 | 5/2000 |
| WO | 0028918 | 5/2000 |
| WO | 0036995 | 6/2000 |
| WO | 0042919 | 7/2000 |
| WO | 0045735 | 8/2000 |
| WO | 0061033 | 10/2000 |
| WO | 0062727 | 10/2000 |
| WO | 0103608 | 1/2001 |
| WO | 0121070 | 3/2001 |
| WO | 0121098 | 3/2001 |
| WO | 0121099 | 3/2001 |
| WO | 0150981 | 7/2001 |

OTHER PUBLICATIONS

Bach et al., "Early Improvement in Congestive Heart Failure after Correction of Secondary Mitral Regurgitation in End-Stage Cardiomyopathy," American Heart Journal, Jun. 1995, pp. 1165-1170.

Schuler et al., "Temporal Response of Left Ventricular Performance of Mitral Valve Surgery," vol. 59, No. 6, Jun. 1979, pp. 1218-1231.

Huikuri, "Effect of Mitral Valve Replacement of Left Ventricular Function in Mitral Regurgitation," Br. Heart J., vol. 49, 1983, pp. 328-333.

Pitarys II et al., "Long-Term Effects of Excision of the Mitral Apparatus on Global and Regional Ventricular Function in Humans," JACC, vol. 15, No. 3, Mar. 1, 1990, pp. 557-563.

Bolling et al., "Surgery for Acquired Heart Disease/Early Outcome of Mitral Valve Reconstruction in Patients with End-Stage Cardiomyopathy," The Journal of Thoracic and Cardiovascular Surgery, vol. 109, No. 4, Apr. 1995, pp. 676-683.

Masahiro et al., "Surgery for Acquired Heart Disease/Effects of Preserving Mitral Apparatus on Ventricular Systolic Function in Mitral Valve Operations in Dogs," The Journal of Thoracic and Cardiovascular Surgery, vol. 106, No. 6, Dec. 1993, pp. 1138-1146.

Dickstein et al., "Heart Reduction Surgery: An Analysis of the Impact on Cardiac Function," The Journal of Thoracic and Cardiovascular Surgery, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency," The Annals of Thoracic Surgery, vol. 46, No. 3, Sep. 1988, 2 pages.

Kurlansky et al., "Adjustable Annuloplasty for Tricuspid Insufficiency," Ann. Thorac. Surg., 44:404-406, Oct. 1987.

Savage, M.D., "Repair of Left Ventricular Aneurysm," The Journal of Thoracic and Cardiovascular Surgery, vol. 104, No. 3, Sep. 1992, pp. 752-762.

Melvin, "Ventricular Radius Reduction Without Restriction: A Computational Analysis," ASAIO Journal, 45:160-165, 1999.

Cox, "Left Ventricular Aneurysms: Pathophysiologic Observations and Standard Resection," Seminars in Thoracic and Cardiovascular Surgery, vol. 9, No. 2, Apr. 1997, pp. 113-122.

Boyd et al., "Tricuspid Annuloplasty," The Journal of Thoracic Cardiovascular Surgery, vol. 68, No. 3, Sep. 1974, 8 pages.

Melvin et al., Reduction of Ventricular Wall Tensile Stress by Geometric Remodeling Device, 1999.

Kay et al., "Surgical Treatment of Mitral Insufficiency", The Journal of Thoracic Surgery, 29:618-620, 1955.

McCarthy, Transcription of Mar. 13, 2000 Presentation.

Acorn Cardiovascular, Inc., "Acorn Cardiovascular Abstracts", Nov. 13, 2000.

Acorn Cardiovascular, Inc., "Acorn Cardiovascular Summary", undated.

Acorn Cardiovascular, Inc., Acorn Cardiovascular Company Overview, Jun. 2000.

Acorn Cardiovascular, Inc., "Acorn Cardiovascular Company Overview", undated.

Acorn Cardiovascular, Inc., Acorn Cardiovascular Business Plan, May 2000.

Acorn Cardiovascular, Inc., "Acorn Cardiovascular Highlights Abstracts", Mar. 10, 1999; Apr. 19, 1999; Oct. 1, 1999; Nov. 9, 1999.

Batista, et al., "Partial Left Ventriculectomy to Treat End-Stage Heart Disease", Ann. Thorac. Surg., 64:634-8, 1997.

Melvin, "Ventricular Radius-Reduction Without Resection A Computational Assessment," undated.

Kay et al., "Surgical Treatment of Mitral Insufficiency", Surgery, 37:697-706, May 1955.

Bailey et al., "The Surgical Correction of Mitral Insufficiency by the Use of Pericardial Grafts," The Journal of Thoracic Surgery, 28:551-603, Dec. 1954.

Bailey et al., "Closed Intracardiac Tactile Surgery," Disease of the Chest, 22:1-24, Jul. 1952.

Harken et al., "The Surgical Correction of Mitral Insufficiency", The Journal of Thoracic Surgery, 28:604-27, 1954.

Harken et al., "The Surgical Correction of Mitral Insufficiency", Surgical Forum, 4:4-7, 1953.

Sakakibara, "A Surgical Approach to the Correction of Mitral Insufficiency", Annals of Surgery, 142:196-203, 1955.

Glenn et al., "The Surgical Treatment of Mitral Insufficiency : The Fate of a Vascularized Transchamber Intracardiac Graft", Annals of Surgery, 141:510-518, Apr. 1955.

Shumacker, Jr., "Attempts to Control Mitral Regurgitation", The Evolution of Cardiac Surgery, 203-210, 1992.

Nation's First "Heart Jacket" Surgery to Treat Heart Failure Performed at HUP: Novel "Cardiac Support Device" Comes to America After Promising Results in Europe, Jun. 26, 2000.

"'Heart Jacket' could help stop heart failure progression," Clinica 916, Jul. 2000.

McCarthy et al., "Device Based Left Ventricular Shape Change Immediately Reduces Left Ventricular Volume and Increases Ejection Fraction in a Pacing Induced Cardiomyopathy Model in Dogs: A Pilot Study," JACC, Feb. 2000, p. 183.

Edie, M.D. et al., "Surgical Repair of Single Ventricle," The Journal of Thoracic and Cardiovascular Surgery, vol. 66, No. 3, Sep. 1973, pp. 350-360.

McGoon, M.D. et al., "Correction of the Univentricular Heart Having Two Atrioventricular Valves," The Journal of Thoracic and Cardiovascular Surgery, vol. 74, No. 2, Aug. 1977, pp. 218-226.
Lev, M.D., et al., "Single (Primitive) Ventricle," Circulation, vol. 39, May 1969, pp. 577-591.
Westaby with Bosher, "Landmarks in Cardiac Surgery," 1997, pp. 198-199.
Shumacker, "Cardiac Aneurysms," The Evolution of Cardiac Surgery, 1992, pp. 159-165.
Feldt, M.D., "Current Status of the Septation Procedure for Univentricular Heart," The Journal of Thoracic and Cardiovascular Surgery, vol. 82, No. 1, Jul. 1981, pp. 93-97.
Doty, M.D., "Septation of the Univentricular Heart," The Journal of Thoracic and Cardiovascular Surgery, vol. 78, No. 3, Sep. 1979, pp. 423-430.
Carpentier et al., "Myocardial Substitution with a Stimulated Skeletal Muscle: First Successful Clinical Case," Letter to the Editor, p. 1267, Sep. 25, 1996.
Ianuzzo et al., "Preservation of the Latissimus Dorsi Muscle During Cardiomyoplasty Surgery," J.Card. Surg., 1996:11:99-108.
Ianuzzo et al., "On Preconditioning of Skeletal Muscle: Application to Dynamic Cardiomyoplasty," Invited Commentary, J. Card. Surg., 1996:11:109-110.
Chachques et al., "Latissimus Dorsi Dynamic Cardiomyoplasty," Ann. Thorac. Surg., 1989:47:600-604.
Moreira et al., "Latissimus Dorsi Cardiomyoplasty in the Treatment of Patients with Dilated Cardiomyopathy," Supplement IV Circulation, Sep. 25, 1996, 7 pgs.
Lucas et al., "Long-Term Follow-Up (12 to 35 Weeks) After Dynamic Cardiomyoplasty," JACC, vol. 22, No. 3, Sep. 1993:758-67.
Batista et al., "Partial Left Ventriculectomy to Improve Left Ventricular Function in End-Stage Heart Disease," J. Card. Surg., 1996:11:96-98.
"Congestive Heart Failure in the United States: A New Epidemic" Data Fact Sheet, National Heart, Lung, and Blood Institute, National Institutes of Health, Dec. 9, 1996, pp. 1-6.
Kormos et al., "Experience with Univentricular Support in Mortally Ill Cardiac Transplant Candidates," Ann. Thorac. Surg., 1990:49:261-71.
Wampler et al., "Treatment of Cardiogenic Shock with the Hemopump Left Ventricular Assist Device," Ann. Thorac. Surg., 1991:52:506-13.
McCarthy et al., "Clinical Experience with the Novacor Ventricular Assist System," J. Thorac. Cardiovasc. Surg., 1991:102-578-87.
Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.
Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.
Bearnson et al., "Development of a Prototype Magnetically Suspended Rotor Ventricular Assist Device," ASAIO Journal, 1996, pp. 275-280.
Sakakibara et al., "A Muscle Powered Cardiac Assist Device for Right Ventricular Support: Total Assist or Partial Assist?." Trans, Am.Soc. Artif. Intern. Organs, vol. XXXVI, 1990, pp. 372-375.
Medtronic, Inc. 1996 Annual Shareholders Report, 79 pages.
ABIOMED, Inc. Annual Report 1996, 32 pages.
Press Release dated Sep. 16, 1996, "ABIOMED Wins $8.5 Million Federal Contract to Qualify its Artificial Heart for Human Trials," 5 pages.
Press Release dated Sep. 26, 1996, ABIOMED's Temporary Artificial Heart System Reaches 200 U.S. Medical Center Milestone, 1 page.
Press Release date May 17, 1996, "ABIOMED Receives FDA Approval to Expand Indications for Use of Cardiac Assist System," 1 page.
Press Release dated Oct. 3, 1995, "ABIOMED Wins $4.35 Million Contract from the National Heart, Lung and Blood Institutes to Develop Implantable Heart Booster," 1 page.
Press Release date Sep. 29, 1995, "ABIOMED" Wins NIH Grant to Develop Calcification-Resistant Plastic Heart Valve, 1 page.
Press Release dated Aug. 25, 1995, "ABIOMED" Wins Research Grant from NIH to Develop Suturing Instrument for Abdominal Surgery, 1 page.
Press Release dated Aug. 11, 1995, "ABIOMED Receives Grant from NIH to Develop Disposable Bearingless Centrifugal Blood Pump," 1 page.
Press Release dated Jun. 9, 1995, "ABIOMED Receives Grant from National Institute of Health to Develop a Laser Welding Technique for Tissue Repair," 1 page.
Press Release dated Apr. 27, 1995, "ABIOMED's Temporary Artificial Heart System Reaches 1,000 Patient Milestone; BVS-5000 in More Than 100 U.S. Medical Centers," 1 page.
"Reversible Cardiomyopathy," Thoratec's Heartbeat, vol. 10.2, Aug. 1996, 4 pages.
Tsai et al., "Surface Modifying Additives for Improved Device-Blood Compatibility," ASAIO Journal, 1994, pp. 619-624.
Farrar et al., "A New Skeletal Muscle Linear-Pull Energy Convertor as a Power Source for Prosthetic Support Devices," The Journal of Heart & Lung Transplantation, vol. 11, No. 5, Sep. 1992, pp. 341-349.
Brochure entitled "Thoratec Ventricular Assist Device System—Because Heart Patients Come in All Sizes," date even with or prior to Jan. 2, 1997, 5 pages.
Press Release dated Oct. 3, 1994, "Heartmate System Becomes First Implantable Cardiac-Assist Device to be Approved for Commercial Sale in the U.S.," 2 pages.
US 6,197,052, 03/2001, Cosgrove et al. (withdrawn)

* cited by examiner

θ > π

θ < π

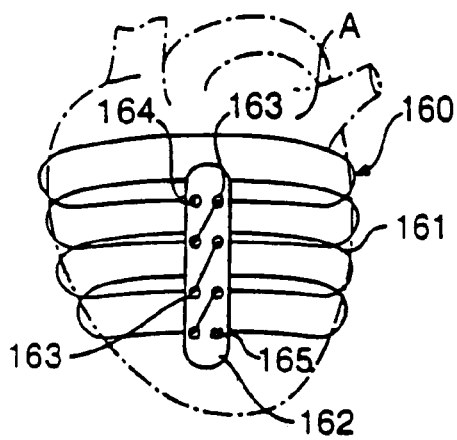
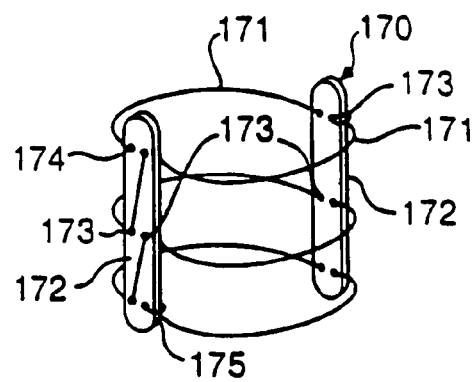
FIG. 26          FIG. 27
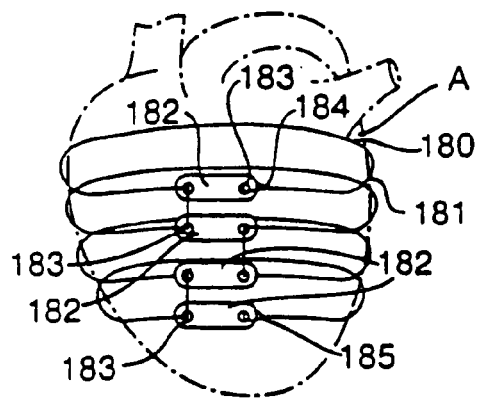
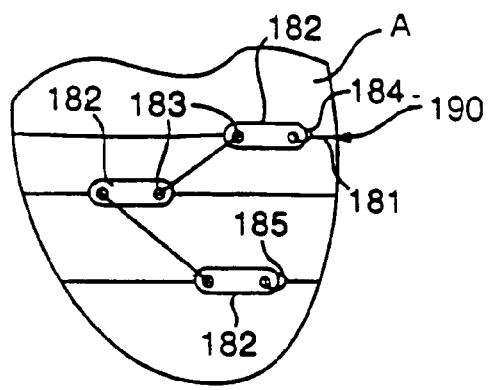
FIG. 28          FIG. 29
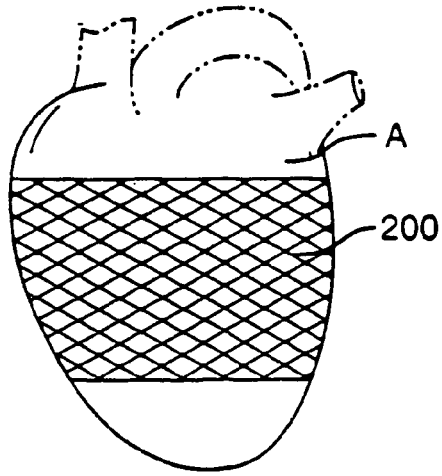
FIG. 30

CHORDAE CAPTURING METHODS FOR STRESS REDUCTION

RELATED APPLICATIONS

This application is a continuation of U.S. application Ser. No. 10/138,520 filed May 6, 2002, now U.S. Pat. No. 6,908,424, which is a continuation of U.S. application Ser. No. 09/843,078 filed Apr. 27, 2001, now U.S. Pat. No. 6,402,680, which is a divisional of U.S. application Ser. No. 09/522,068, filed Mar. 9, 2000, now U.S. Pat. No. 6,264,602, which is a continuation of U.S. application Ser. No. 09/124,321, filed Jul. 29, 1998, now U.S. Pat. No. 6,077,214, the entire disclosure of each being incorporated by reference herein. This application is related to U.S. application Ser. No. 09/123,977, filed on Jul. 29, 1998, now U.S. Pat. No. 6,260,552, and entitled "Transventricular Implant Tools and Devices" and U.S. application Ser. No. 09/124,286, filed on Jul. 29, 1998, now U.S. Pat. No. 6,045,497, and entitled "Heart Wall Tension Reduction Apparatus and Method," both of which are incorporated herein by reference.

FIELD OF THE INVENTION

The present invention pertains to the field of apparatus for treatment of a failing heart. In particular, the apparatus of the present invention is directed toward reducing the wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of ventricular dilation and myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes such as digoxin are cardiac glycosides and function to increase cardiac output by increasing the force and speed of cardiac muscle contraction. These drug therapies offer some beneficial effects but do not stop the progression of the disease.

Assist devices include, for example, mechanical pumps. Mechanical pumps reduce the load on the heart by performing all or part of the pumping function normally done by the heart. Currently, mechanical pumps are used to sustain the patient while a donor heart for transplantation becomes available for the patient.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a device and method for reducing mechanical heart wall muscle stress. Heart muscle stress is a stimulus for the initiation and progressive enlargement of the left ventricle in heart failure. Reduction of heart wall stress with the devices and methods disclosed herein is anticipated to substantially slow, stop or reverse the heart failure disease process. Although the primary focus of the discussion of the devices and methods of the present invention herein relates to heart failure and the left ventricle, these devices and method could be used to reduce stress in the heart's other chambers.

The devices and methods of the present invention can reduce heart wall stress throughout the cardiac cycle including end diastole and end systole. Alternatively, they can be used to reduce wall stress during the portions of the cardiac cycle not including end systole. Those devices which operate throughout the cardiac cycle are referred to herein as "full cycle splints". Those devices which do not operate to reduce wall stress during end stage systole are referred to as "restrictive devices". Restrictive devices include both "restrictive splints" which alter the geometric shape of the left ventricle, and "wraps" which merely limit the magnitude of the expansion of the left ventricle during diastolic filling without a substantial shape change.

While it is desirable to reduce wall stress for the treatment of heart failure, to slow or reverse the disease process and to increase heart wall muscle shortening and pumping efficiency, it is also desirable to maintain or improve stroke volume and allow for variable preload.

Improving muscle shortening both total length change and extent at end systole, is particularly important in symptomatic heart failure wherein the heart has decreased left ventricle function and has enlarged. Full cycle splinting can be used to obtain a substantial increase in muscle shortening. Improved shortening will lead to an increase in pump function, and chronically may result in muscle strengthening and reversal of the disease because of increased pumping efficiency. The increase in shortening should be balanced against a reduction in chamber volume.

In asymtomatic, early stage heart failure, it may be possible to use only a restrictive device or method as elevated wall stress is considered to be an initiator of muscle damage and chamber enlargement. Restrictive devices and methods acting during diastole will reduce the maximum wall stress experience during end diastole and early systole. It should be understood that restrictive devices and methods can be used in combination with full cycle splinting to more precisely control or manipulate stress reduction throughout the cardiac cycle.

BRIEF DESCRIPTION OF THE DRAWINGS

FIG. 26 is a vertical view of a heart in phantom line including a single element wrap including longitudinal axis securing points;

FIG. 27 is an alternate embodiment of the wrap of FIG. 26;

FIG. 28 is an alternate embodiment of the wrap of FIG. 26;

FIG. 29 is an alternate embodiment of the wrap of FIG. 26;

FIG. 30 is a vertical view of the heart including a mesh wrap;

DETAILED DESCRIPTION OF THE PREFERRED EMBODIMENTS

Figure 1:
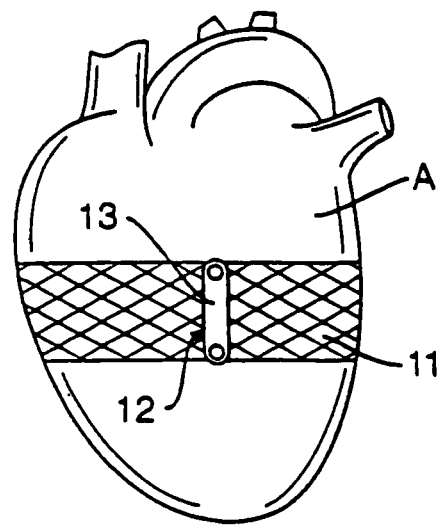
FIG. 1 is a vertical side view of a heart including a transventricular splint and band splint.

The present invention is directed at reducing wall stress in a failing heart Diastolic wall stress is considered to be an initiator of muscle damage and chamber enlargement. For this reason, it is desirable to reduce diastolic wall stress to prevent the progression of the disease. The significant impact of stress occurs at all stages and functional levels of heart failure, however, independent of the original causes. For example, in asymtomatic early stages of heart failure mechanical stress can lead to symptomatic heart failure marked by an enlarged heart with decreased left ventricle function. As the heart enlarges, mechanical stress on the heart wall increases proportionally to the increasing radius of the heart in accordance with LaPlace's Law. It can thus be appreciated that as stress increases in symptomatic heart failure, those factors that contributed to increasing stress also increase. Thus, the progression of the disease accelerates to late stage heart failure, end stage heart failure and death unless the disease is treated.

Three parameters influence mechanical stress on the muscle. These are: (I) muscle mass, i.e., as reflected by the thickness of the muscle; (2) pressure in the chamber which is a function of the resistance to blood flow of the patient's vasculature and the volume of blood within the patient; and (3) chamber of geometry. The present invention pertains to devices and methods for directly and passively changing chamber geometry to lower wall stress. In addition to treatment of heart failure, the devices and methods of the present invention also lend themselves to application in the case of a decrease in cardiac function caused by, for example, acute myocardial infarction.

The device's disclosed herein for changing chamber geometry are referred to as "splints". In addition to splints, wraps which can be placed around the heart can limit muscle stress without the chamber shape change. When a wrap is used, wall stress is merely transferred to the wrap, while the generally globular shape of the heart is maintained. A wrap could be used in conjunction with a splint to modulate heart wall stress reduction at various stages of the cardiac cycle.

The present invention includes a number of splint embodiments. Splints and wraps can be classified by where in the cardiac cycle they engage the heart wall, i.e., mechanically limit the size of the left ventricle in the case of wraps and change the geometry of the ventricle in the case of splints. If a splint or wrap only begins to engage during diastolic filling, the splint can be termed a "restrictive splint". If the splint or wrap is engaged throughout the cardiac cycle, both during diastolic filling and systolic contraction and ejection, the splint can be termed a "full cycle splint". The wrap will generally be a restrictive device which begins to engage during diastolic filling to increase the elastance (reduces compliance) of the chamber. If a wrap is made from elastic material it may engage full cycle, but the force required to elongate the wrap will increase as diastolic filling progresses, preload strain will be reduced without an improvement in systolic contraction.

Figure 2:
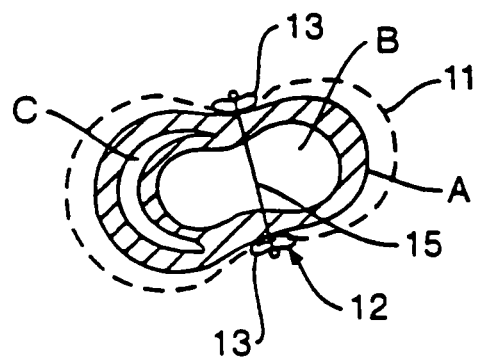
FIG. 2 is a horizontal cross section of the heart, splint and band splint of FIG. 1.

FIG. 1 is a view of a heart A in a normal, generally vertical orientation. A wrap 11 surrounds heart A and a transventricular splint 12 extends through the heart and includes an anchor or anchor pad 13 disposed on opposite sides of the heart. FIG. 2 is a horizontal cross sectional view of heart A taken through wrap 11 and splint 12. Splint 12 includes a tension member 15 extending through left ventricle B. Anchor pads 13 are disposed at each end of tension member 15. Right ventricle C is to the left of left ventricle B.

In FIG. 1, wrap 11 and splint 12 are shown engaged with heart A. In FIG. 2, heart A is shown spaced from wrap 11 except at anchor pads 13. In FIG. 2, heart A is thus at a point in the cardiac cycle where the muscles are shortening during systole, or have yet to stretch sufficiently during diastolic expansion to reach wrap 11. Accordingly, wrap 11 can be considered a restrictive device as it does not engage the heart full cycle. Although wrap 11 is in contact with heart A at pads 13, only the splint is providing a compressive force to change the shape of the heart and limiting the stress of the heart in FIG. 2.

If heart A, as shown in FIG. 2 is at end systole, transventricular splint 12 is a full cycle device as the cross section of left ventricle B does not have the generally circular unsplinted shape. It can be appreciated that transventricular splint 12 can be used without wrap 11. Alternately, wrap 11 could be secured to heart A by sutures or other means than splint 12, in which case wrap 11 would be merely a restrictive device. It should be noted that unless wrap 11 extends vertically along heart A a sufficient amount, as heart A expands and engages wrap 11, the portion of left ventricle B disposed above or below wrap 11 could expand substantially further than that portion of the left ventricle wall restrained by wrap 11. In such a case, left ventricle B could have a bi-lobed shape in a vertical cross section. As such, the wrap 11 would not be merely limiting the size of the left ventricle, but rather inducing a shape change in the left ventricle. In such a case, the element 11 would not be a wrap, but rather a splint which could be referred to as a "band splint".

Each of the splints, wraps and other devices disclosed in this application preferably do not substantially deform during the cardiac cycle such that the magnitude of the resistance to the expansion or contraction of the heart provided by these devices is reduced by substantial deflection. It is, however, contemplated that devices which deflect or elongate elastically under load are within the scope of the present invention, though not preferred. The materials from which each device are formed must be biocompatible and are preferably configured to be substantially atraumatic.

Figure 3:
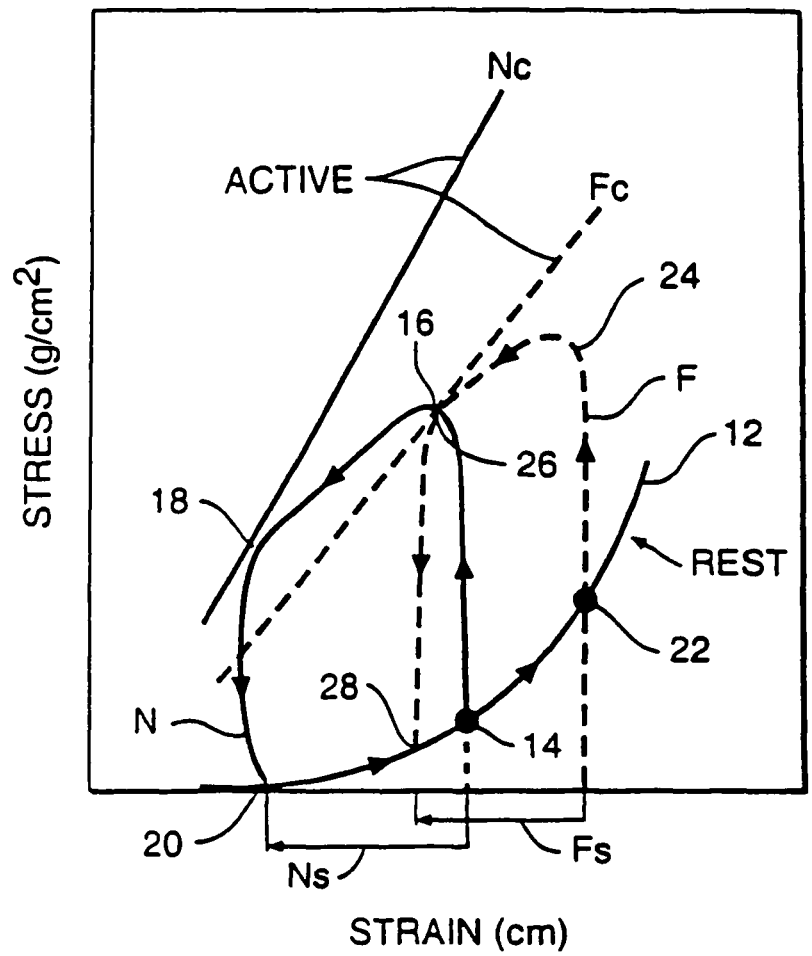
FIG. 3 is a graph showing the relationship between stress and strain for the sarcomeres of the left ventricle for a normal and failing heart throughout the cardiac cycle.

The distinction between restrictive devices, such as restrictive splints and wraps, and full cycle splints and wraps, can be better understood by reference to FIG. 3. FIG. 3 is a plot of sarcomere, i.e., heart wall muscle, stress in $(g/cm^2)$ versus strain throughout a normal cardiac cycle N, and a failing heart cardiac cycle F. The cardiac cycles or loops shown on FIG. 3 are bounded by the normal contractility curve $N_c$ and failing heart contractility curve $F_c$ above and to the left, and the diastolic filling curve 12 toward the bottom and right. Contractility is a measure of muscle stress at an attainable systolic stress at a given elongation or strain. It can be appreciated that the muscle contractility $N_c$ of normal muscle tissue is greater than the contractility $F_c$ of the muscle tissue of a failing heart. The diastolic filling curve 12 is a plot of the stress in the muscle tissue at a given elongation or strain when the muscle is at rest.

An arbitrary beginning of the normal cardiac cycle N can be chosen at end diastole 14, where the left ventricle is full, the aortic valve is closed. Just after end diastole 14, systole begins, the sarcomere muscles become active and the mitral valve closes, increasing muscle stress without substantially shortening (sometimes referred to as "isovolurnic contraction"). Stress increases until the aortic valve opens at 16. Isotonic shortening begins and stress decreases and the muscles shorten until end systole 18, where the blood has been ejected from the left ventricle and the aortic valve closes. After end systole 18, diastole begins, the muscles relax without elongating until diastolic filling begins when the mitral valve opens at 20. The muscles then elongate while the mitral valve remains open during diastolic filling until end diastole 14. The total muscle shortening and lengthening during the normal cycle N is $N_s$.

An analogous cycle F also occurs in a failing heart. As the left ventricle has dilated, in accordance with LaPlace's Law, the larger radius of a dilated left ventricle causes stress to increase at a given blood pressure. Consequently, a failing heart must compensate to maintain the blood pressure. The compensation for the increased stress is reflected in the shift to the right of failing heart cardiac cycle F relative to the normal cycle N. The stress at end diastole 22 is elevated over the stress at end diastole 14 of the normal heart. A similar increase can be seen for the point at which the aortic valve opens 24, end systole 26 and the beginning of diastolic filling 28 relative to the analogous points for the normal cycle N. Muscle shortening and elongation F, throughout the cycle is also reduced in view of the relative steepening of the diastolic curve 12 to the right and the flatter contractility curve $F_c$ relative to the normal contractility $N_c$.

By reference to the heart cycle stress strain graph of FIG. 3, the effect on mechanical muscle stress and strain caused by the use of the devices and methods of the present invention can be illustrated. Restrictive devices begin to engage during diastolic filling, which in the case of a failing heart occurs along diastolic filling curve 12 between point 28 and 22. Restrictive devices do not engage at end systole 26. Thus, the acute effect of placement of a restrictive device is to reduce muscle stress at end diastole relative to the stress at point 22, and shift the line 22-24 to the left reducing muscle shortening and elongation $F_s$. Acutely, the cardiac cycle will still operate between the failing heart contractility curve $F_c$ and the diastolic filling curve 12. If chronic muscle contractility increases such that the muscle contractility curve $F_c$ shifts back toward the normal heart contractility curve Nc as a consequence of the stress reduction, the stress/strain curve F of the cardiac cycle will shift to the left reducing mechanical stress still further.

The effect on the stress/strain relationship of a full cycle splint will acutely shift the entire stress/strain curve F for the cycle to the left. That is, stress is reduced at both end diastole 22 and end systole 26. Muscle shortening and elongation $F_s$ will increase acutely. If, as in the case of a restrictive splint, muscle contractility $F_c$ improves, the entire cardiac cycle curve F will shift further to the left reducing mechanical stress still further.

The type and magnitude of shape change are important factors in determining the effectiveness of splinting. There are several types of lower stress cardiac geometries that can be created from an enlarged globular left ventricular chamber typically associate with heart failure. They include lobed, disc-like, narrowed elongate, and multiple vertically stacked bulbs.

Figure 4:
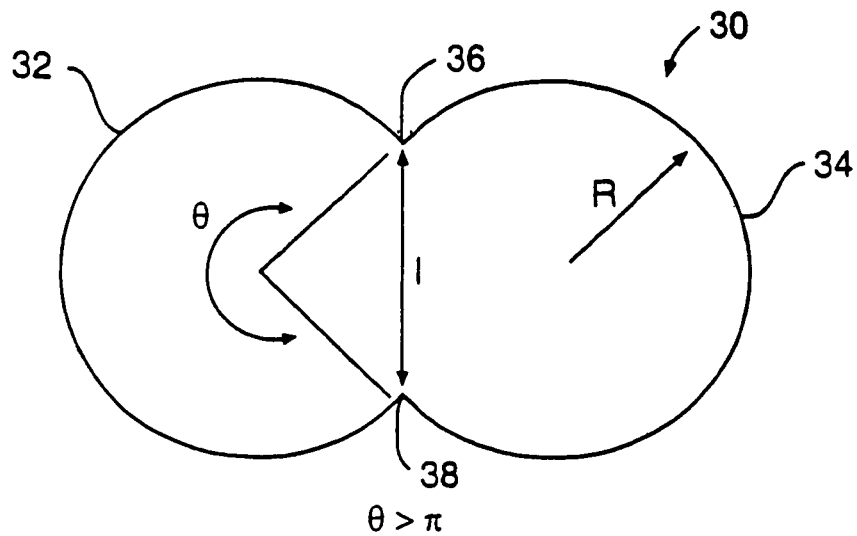
FIG. 4 is an idealized horizontal cross section of a left ventricle splinted to form two lobes.

FIG. 4 shows an idealized horizontal cross section of a left ventricle 30 subdivided into two symmetrical lobes 32 and 34 having an arc passing through an angle $\theta>\pi$, and a radius R. Lobes 32 and 34 can be formed using a splint, such as transventricular splint 12 shown in FIGS. 1 and 2. Lobes 32 and 34 are joined at points 36 and 38. Points 36 and 38 are separated by a distance l.

Figure 5:
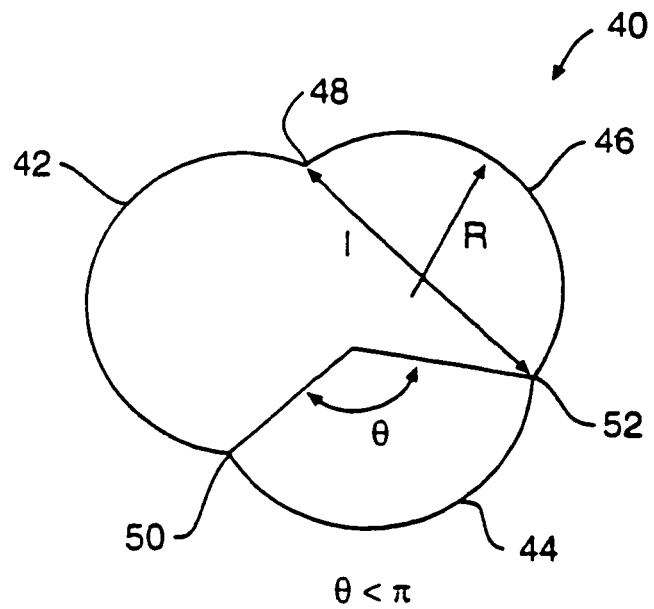
FIG. 5 is an idealized horizontal cross sectional left ventricle splinted to form three lobes.

FIG. 5 is an idealized horizontal cross section of a left ventricle 40 subdivided into three generally equal sized lobes 42, 44 and 46. Each lobe has an equal radius and has an arc passing through an angle less than $\pi$. Adjacent ends of the lobes 48, 50 and 52 are separated by a distance l. A plurality of transventricular splints such as splint 12 as shown in FIGS. 1 and 2 could be extended between adjacent ends 48, 50 and 52 to form lobes 42, 44 and 46.

For a restrictive splint, the horizontal cross sections 30 and 40 will have a generally circular shape, i.e., a non-splinted shape at end systole. As diastolic filling proceeds, the radius of the circular shape will continue to increase until the splint engages. At the point the splint engages, the lobed shape will begin to form. In the case of the two lobe splinting of FIG. 4, the radius will continue to increase as diastolic filling proceeds. In the case of the three or more lobed shape, such as the three lobed configuration of FIG. 5, radius R will decrease as diastolic filling proceeds. The radius will continue to decrease unless or until the pressure in the heart causes the heart to expand such that the arc of the lobe passes through an angle $\theta$ greater than $\pi$.

In the case of a full cycle splint, at end systole, the splint will already be engaged. Thus, for a full cycle splint at end systole, the horizontal cross section of the chamber will not have the normal generally circular shape. Rather, at end systole, the horizontal cross sections 30 and 40 will have a lobed shape such as shown in FIGS. 4 and 5. Subsequent shape change during diastolic filling for a full cycle splint will be similar to that described with respect to restrictive splints.

In view of LaPlace's Law which states that stress is directly proportional to radius of curvature, it can be appreciated that whether the radius is increasing or decreasing during diastolic filling, will have an impact on heart pumping performance. Where R is increasing during diastolic filling, wall stress will increase more rapidly than where R is decreasing. The number of lobes that are created can significantly influence the level of end diastolic muscle stress reduction achieved through splinting. Eventually adding additional lobes forms a configuration which approaches a behavior similar to a wrap. If a wrap is substantially inelastic, or of sufficient size, a wrap will only engage the heart wall at some stage of diastolic filling. If the wrap is substantially inelastic, as pressure increases in the chamber during diastolic filling, stress in the heart wall muscle will increase until the wrap fully engages and substantially all additional muscle elongating load created by increased chamber pressure will be shifted to the wrap. No further elongation of the chamber muscles disposed in a horizontal cross section through the wrap and the chamber will occur. Thus, inelastic wraps will halt additional preload muscle strain (end diastolic muscle stretch).

The type of shape change illustrated in FIGS. 4 and 5 is of substantial significance for restrictive splints. It is undesirable in the case of restrictive splints, to excessively limit preload muscle strain. The Frank-Starling Curve demonstrates the dependence and need for variable preload muscle strain on overall heart pumping performance. During a person's normal activities, their body may need increased blood perfusion, for example, during exertion. In response to increased blood perfusion through a person's tissue, the heart will compensate for the additional demand by increasing stroke volume and/or heart rate. When stroke volume is increased, the patient's normal preload strain is also increased. That is, the lines 14-16 and 22-24 of the normal and failing hearts, respectively, will shift to the right. An inelastic wrap will, at engagement, substantially stop this shift. In the case of the bi-load shape change of FIG. 4 or a multiple lobed change having a small number of lobes of FIG. 5, significant stress reduction can be achieved while allowing for variable preload strain. If the number of lobes is increased substantially, however, variable preload will decrease as the multi-lobed configuration approaches the performance of an inelastic wrap.

The magnitude of shape change in the case of full cycle splinting becomes very important as full cycle splinting generally reduces chamber volume more than restrictive splinting. Although as with restrictive devices, the type of shape change is also important to allow for variable preload strain. Both restrictive device and full cycle splints reduce chamber volume as they reduce the cross sectional area of the chamber during the cardiac cycle. The magnitude of the shape change can vary from very slight at end diastole, such that chamber volume is only slightly reduced from the unsplinted end diastolic volume, to an extreme reduction in volume, for example, complete bifurcation by transventricular splint. The magnitude of the shape change, for example, as measured by the ratio of splint length to non-splinted ventricular diameter, is preferably modulated to reduce muscle stress while not overly reducing chamber volume. For full cycle splint, the reduction of chamber volume is compensated for by increased contractile shortening, which in turn leads to an increased ejection fraction, i.e., the ratio of the stroke volume to chamber volume. For given stress/volume and stress/shortening relationships, there will be a theoretical optimum maximal stroke volume. Clinically, 20% to 30% stress reduction is expected to be attainable through full cycle bi-lobe splinting. See U.S. patent application Ser. No. 08/933,456, filed Sep. 18, 1997 for calculation of stress reduction for idealized bi-lobe splinting.

When using the full cycle and restrictive devices described herein, caution should be exercised to limit the pressure on the coronary vasculature. In the case of transventricular splints, valve structure, electrical pathways and coronary vasculature should be avoided.

Figure 6:
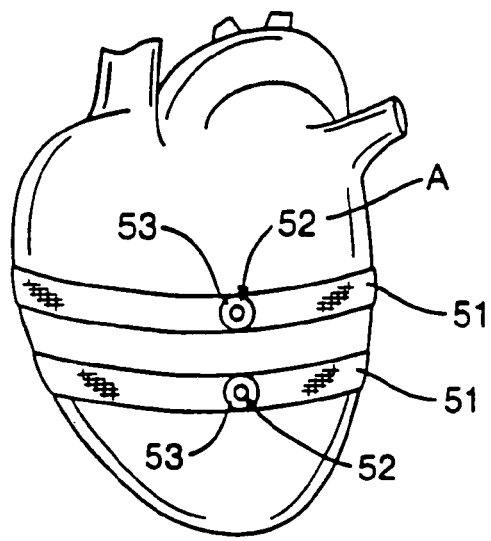
FIG. 6 is a vertical view of a heart including two transventricular splints and two band splints.
Figure 7:
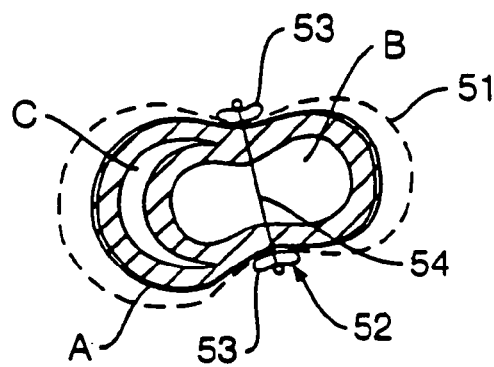
FIG. 7 is a cross sectional view of the heart, a band splint and a splint of FIG. 6.

FIG. 6 is a vertical view of a heart A similar to that shown in FIG. 1. Rather than having a single band splints surrounding heart A, there are two band splints 51 affixed to the heart by two transventricular splints 52. Splints 52 include oppositely disposed anchors or anchor pads 53. FIG. 7 is a horizontal cross sectional view of heart A of FIG. 6, wraps 51 and splint 52. Splints 52 include a tension member 54 disposed through left ventricle B. Pads 53 are disposed on the opposite ends of tension members 54. Right ventricle C is shown to the left of left ventricle B.

Splints 52 can be restrictive or full cycle splints. Band Splints 51 are shown as restrictive band splints as in FIG. 6, heart A is shown engaged with the band splints 51, where as in FIG. 7, heart A has contracted to move away from band splints 51. Wraps 51 and splints 52 should be made from biocompatible materials. Band Splints 51 are preferably made from a pliable fabric or other material which resists elongation under normal operating loads. Band splints 51 can, however, be made from an elastic material which elongates during the cardiac cycle. Tension members 54 also preferably resist elongation under normal operating loads. Tension members 54 can, however, be made from an elastic material which elongates during the cardiac cycle.

Figure 8:
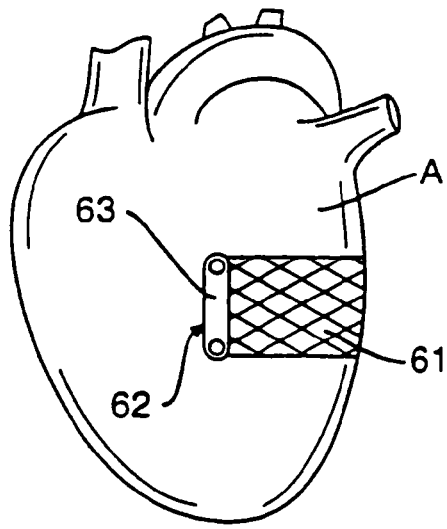
FIG. 8 is a vertical view of a heart including a transventricular splint and a partial band splint.
Figure 9:
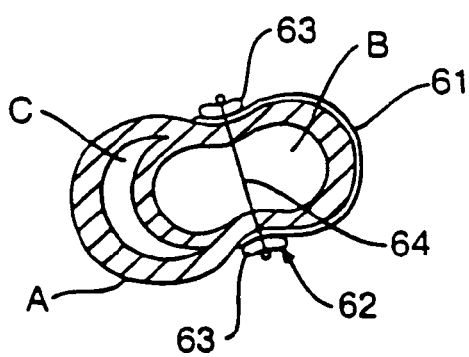
FIG. 9 is a horizontal cross sectional view of the heart, splint and band splint of FIG. 8.

FIG. 8 is a vertical view of heart A, partial wrap 61 and transventricular splint 62. Transventricular splint 62 includes anchor pads 63. FIG. 9 is a horizontal cross sectional view of heart A, partial band splint 61 and splint 62. Splint 62 is essentially similar to wrap or band splint 12 shown in FIGS. 1 and 2. Partial band splint 61 is also essentially similar to wrap or band splint 11 shown in FIGS. 1 and 2 except that band splint 61 only surrounds a portion of heart A. This portion is shown in FIGS. 8 and 9 to the left including a portion of left ventricle B.

Figure 10:
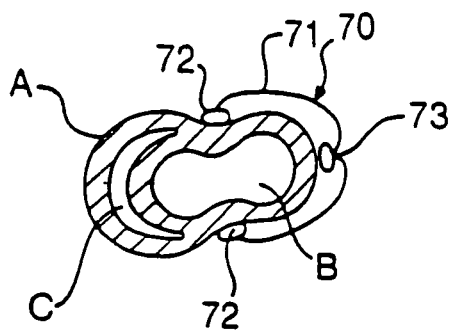
FIG. 10 is a horizontal cross section of a heart including a splint having full cycle and restrictive elements at the beginning of diastolic filling.

FIG. 10 is a horizontal cross sectional view of left ventricle B and right ventricle C of heart A taken at a similar elevation as that shown in FIG. 2. A splint 70 is shown disposed on heart A. Splint 70 includes a frame having two heart engaging anchors or pads 72 disposed at its opposite ends. A third heart engaging pad 73 is disposed along frame 70 approximately midway between pads 72.

Figure 11:
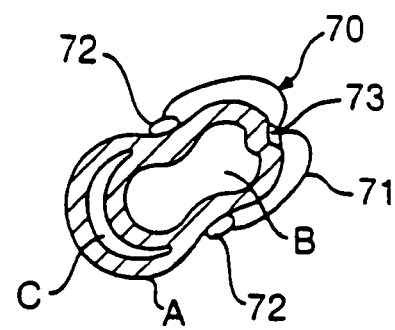
FIG. 11 is a view of the splint of FIG. 10 at end diastole.

Pads 72 are shown engaged with heart A to change the shape of ventricle B in FIG. 10. Pads 73 are not engaged with heart A in FIG. 10. FIG. 11 is the same horizontal cross sectional view as FIG. 10 except that heart A has to contact pad 73 to create a further shape change of left ventricle B.

Frame 70 is preferably rigid enough that pads 72 could be disposed on the heart for full cycle splinting and sufficiently adjustable that pads 72 could be spaced further apart for restrictive splinting. Pad 73 accomplishes restrictive splinting. Frame 71, pads 72 and 73 of splint 70 are made of a biocompatible material. Pads 72 and 73 are preferably substantially atraumatic.

Figure 12:
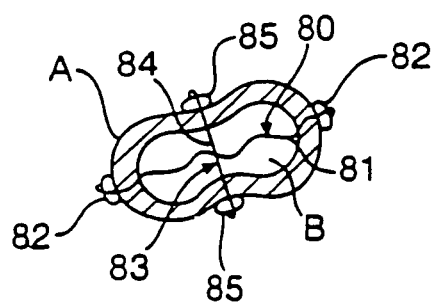
FIG. 12 is a horizontal cross section of the left ventricle including a full cycle transventricular splint and a restrictive transventricular splint at the beginning of diastolic filling.

FIG. 12 is a horizontal cross sectional view of the left ventricle B of heart A. A transventricular splint 80 having a tension member 81 and oppositely disposed anchor pads 82 is shown extending across left ventricle B. Another transventricular splint 83 having a tension member 84 and oppositely disposed anchor pads 85 extends generally perpendicularly to splint 80, across left ventricle B.

Figure 13:
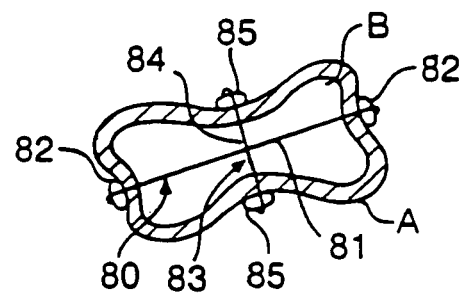
FIG. 13 is a view of the splints of FIG. 12 at end diastole.

It can be appreciated that in FIG. 12 splint 83 is engaging heart A to deform left ventricle B. Splint 80, however, includes a tension member 81 made of a flexible filament, line or the like which is shown in a relaxed state in FIG. 12. In FIG. 13, tension member 81 is shown in an elongated, taunt configuration as heart A has expanded into engagement with pads 82.

Transventricular splints 80 and 83 can be made as described above with respect to the transventricular splint of FIGS. 1 and 2. Tension member 81 may be elastic or inelastic.

Figure 14:
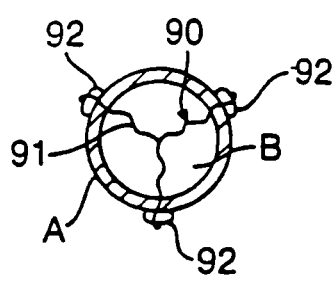
FIG. 14 is a horizontal cross sectional view of the left ventricle including a restrictive splint at the beginning of diastolic filling.

FIG. 14 is a horizontal cross section of left ventricle B of heart A including a transventricular splint 90. Splint 90 includes a tension member 91 including three branches extending to atraumatic anchors or anchor pads 92. Similarly to tension member 81 of FIG. 12, tension member 90 is shown in a relaxed state. Splint 90 can be made in a similar way as splint 80 of FIGS. 12 and 13.

Figure 15:
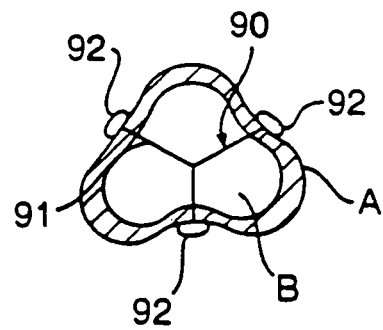
FIG. 15 is a view of the splint of FIG. 14 at end diastole.

FIG. 15 is the same horizontal cross section of heart A as shown in FIG. 14 except that heart A has expanded to engage atraumatic pads 92 of splint 90. Tension member 91 is now drawn taunt to form a three lobed cross sectional configuration of left ventricle B.

Figure 16:
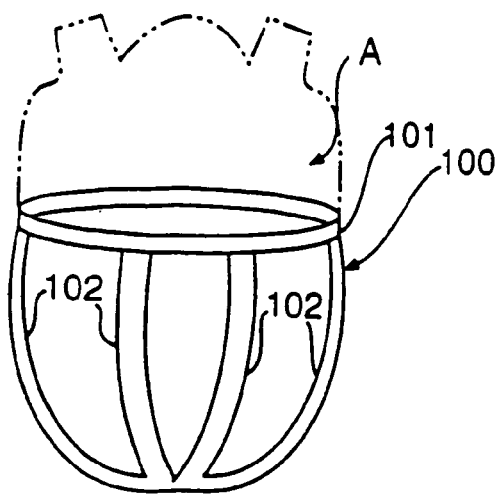
FIG. 16 is a vertical view of the heart in phantom line including a band splint.

FIG. 16 is a vertical view of heart A shown in phantom line. Shown disposed about the ventricles of heart A is a basket-like band splint 100. Band splint 100 includes a horizontal encircling band 101 around an upper region of the ventricles and four bands 102 which extend downward toward the apex of heart A. It can be appreciated that bands 102 can act as splints to form four lobes in heart A in a horizontal plane. Depending on the placement of bands 102 around heart A, lobes could be created only in the left ventricle or in the left ventricle and/or other chambers of the heart. Band 102 is joined at the apex Band 101 and band 102 can be made from a webbing, fabric or other biocompatible material.

If band splint 100 substantially elongated elastically under normal operating loads, it could be friction fit to heart A and act full cycle, limiting muscle stress at end diastole as well end systole. Band splint 100 could be sutured into place or otherwise held on heart A and act as a restrictive device. If band 101 were securely fastened to heart A, bands 102 could limit the vertical elongation of heart A during diastolic filling.

Figure 17:
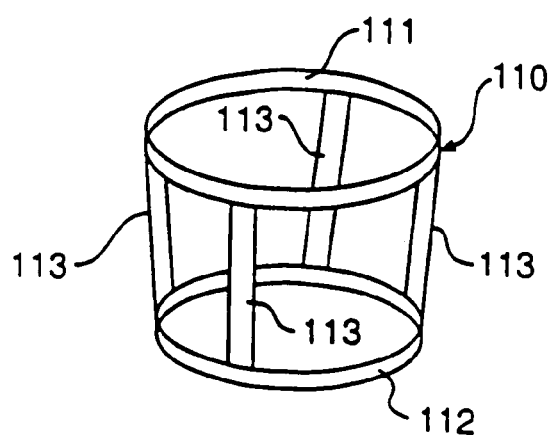
FIG. 17 is an alternate embodiment of the band splint of FIG. 16.

FIG. 17 is an alternate embodiment 110 of the band splint of FIG. 16. Band splint 110 includes a horizontally heart encircling band 111 and four bands 113 extending downward from band 111. Bands 113, however, unlike bands 102 of band splint 100 do not extend to the apex of heart A, but rather to a second horizontally heart encircling band 112.

Band splint 110 could be made of the same materials as band splint 100. Band splint 110 can also be used in a manner similar to band splint 100 except that band splint 110 would limit the vertical elongation of the ventricles less than band splint 100.

Figure 18:
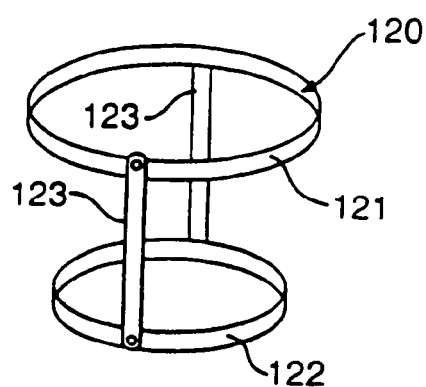
FIG. 18 is an alternate embodiment of the band splint of FIG. 16.

FIG. 18 is yet another alternate embodiment 120 of the wrap of FIG. 16. Band splint 120 closely resembles alternate embodiment 110 of FIG. 17, except that rather than having four vertically extending web members, band splint 120 includes two substantially rigid members 123 interconnecting two horizontally encircling web members 121 and 122.

Figure 19:
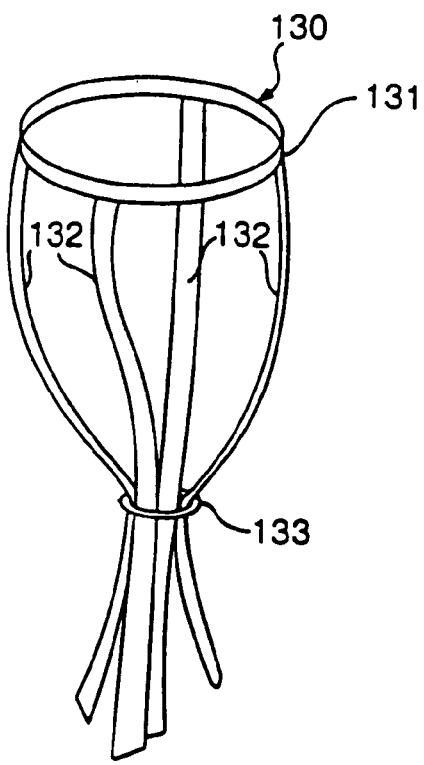
FIG. 19 is an alternate embodiment of the band splint of FIG. 16.

FIG. 19 is yet another alternate embodiment 130 of the band splint of FIG. 16. Like the wrap of FIG. 16, band splint 130 includes a horizontally encircling member 131 and four downwardly extending members 132. At a location proximate of the apex of heart A, members 132 are joined by a ring 133. Members 132 extend through ring 133. Ring 133 can be used to adjust the length of members 132 between band 131 and ring 133. Ring 133 can be formed from metallic material and crimped inwardly to fix its position along members 132. Other means of holding ring 133 in position would be readily apparent to those skilled in the art.

Figure 20:
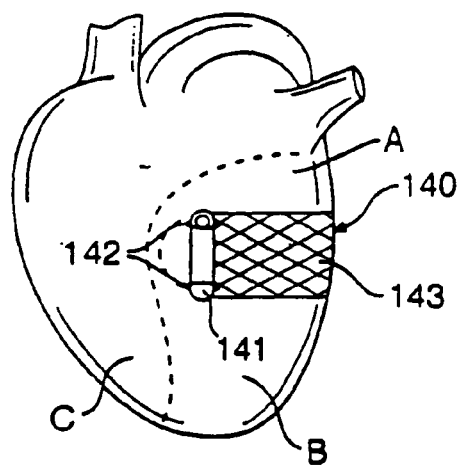
FIG. 20 is a vertical view of a heart including a partial circumferential strap.

FIG. 20 is a vertical view of heart A including a partial band splint 140 secured around a substantial portion of left ventricle B. Band splint 140 includes a vertically elongating anchor member 141 which sutures 142 can encircle to anchor member 141 to heart A. A band 143 extends generally horizontally from anchor member 141 to an opposite anchor 141.

Figure 21:
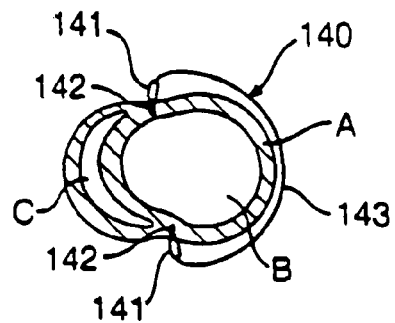
FIG. 21 is a horizontal cross sectional view of the heart and strap of FIG. 20.

The length of band 143 can be seen in its entirety in FIG. 21 which is a horizontal cross sectional view of heart A through band 143, left ventricle B and right ventricle C. In FIG. 20, heart A is shown engaged with band 143, however, in FIG. 21, band 143 is shown spaced from heart A. Thus, in this configuration, wrap 140 would be acting as a restrictive device. If band splint 140 were made from a material that substantially deforms elastically under normal loads, band splint 140 could also be secured sufficiently snuggly to heart A to act as a full cycle device. Preferably, however, band 143 of band splint 140 is formed from a webbing or substantially inelastic fabric.

Figure 22:
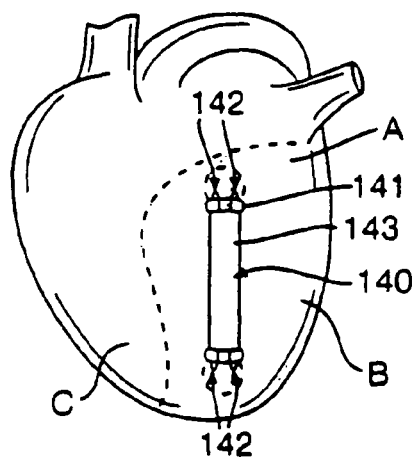
FIG. 22 is a vertical view of a heart including a vertical partial strap.

FIG. 22 is a vertical view of heart A including band splint 140 disposed vertically on left ventricle B. In this position, band splint 140 can limit the vertical elongation of left ventricle B during diastolic filling.

Figure 23:
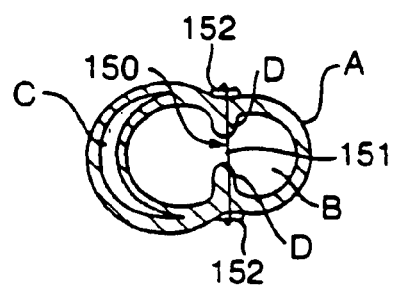
FIG. 23 is a horizontal cross sectional view of a heart including a transventricular splint passing through the papillary muscles.
Figure 24:
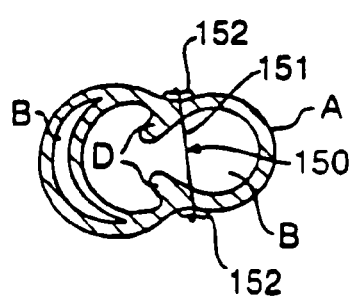
FIG. 24 is a horizontal cross sectional view of a heart including a transventricular splint passing through the left ventricle to lateral the papillary muscles.

FIG. 23 is a horizontal cross section of heart A through left ventricle B, right ventricle C and the papillary muscles D of left ventricle B. A transventricular splint 150 including an elongate tension member 151 and oppositely disposed anchor pads 152 extends through left ventricle B and papillary muscles D. Splint 150 could be similar to splint 12 of FIGS. 1 and 2. FIG. 24 is a horizontal cross section similar to that of FIG. 23. In FIG. 24, however, transventricular splint 150 is shown avoiding papillary muscles D.

Figure 25:
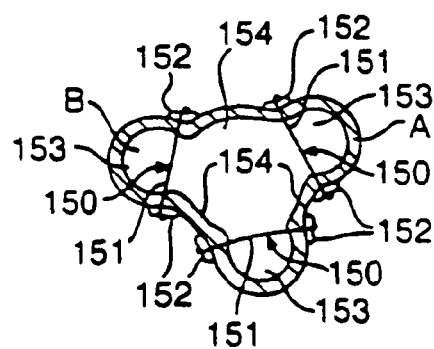
FIG. 25 is a horizontal cross sectional view of the left ventricle including a plurality of transventricular splints.

FIG. 25 is a horizontal cross section of left ventricle B of heart A. Here three splints 150 have been placed to form six lobes. Three of the lobes 153 have an arc length which passes through an angle greater than π. Disposed between each lobe 153 are three lobes 154 which have an arc length which passes through an angle less than π. Consequently, during diastolic filling, the effective radius of lobes 153 will be increasing while the radius of lobes 154 will be decreasing.

FIG. 26 is a vertical view of heart A including a wrap 160. Wrap 160 can include a single thread or line 161 encircling the heart several times. After line 161 encircles heart A, line 161 can be threaded through a bar 162, including a plurality of eyelets 163 spaced along its length in pairs. Bar 162 is preferably rigid enough to substantially maintain the distance between eyelets 163 under normal operating loads.

When line 161 is placed in heart A, one end of line 161 can be tied to bar 162 at 164. Line 161 can then encircle the heart and be drawn through eyelet 162 adjacent the beginning of line 161 at 164. Line 161 can then be drawn through one eyelet 163 of a lower pair of eyelets to encircle the heart again. This process continues until line 161 is tied to an eyelet 163 at 165. It can be appreciated that wrap 160 could be used as a restrictive or full cycle device depending on the diameter of loop formed by line 161.

FIG. 27 is an alternate embodiment 170 of the wrap of FIG. 26. Wrap 170, however, includes two vertically extending bars 172 having eyelets 173 through which line 171 is threaded. Line 171 can be tied to one of the bars 172 at 174 and 175.

FIG. 28 is a vertical view of heart A including yet another embodiment 180 of the wrap of FIG. 26. Wrap 180 includes a line 181 encircling heart A a plurality of times. Rather than having a single vertically extending bar 162 to position line 180 on heart A, wrap 180 includes a plurality of horizontal bars 182 including a pair of eyelets 183. One end of line 181 is tied to an upper bar 182 at 184 and the opposite end of line 181 is tied to a lower bar 182 at 185. Between 184 and 185, line 181 is threaded through eyelets 182 to form the heart encircling pattern shown in FIG. 28.

FIG. 29 is a vertical view of heart A including yet another alternate embodiment 190 of the wrap of FIG. 26. Wrap 190 closely resembles 180 of FIG. 28. Line 181 has, however, been threaded through eyelets 183 of bars 182 in a pattern which, unlike that of FIG. 28, bars 182 are disposed at various selected locations around the circumference of heart A.

FIG. 30 is a vertical view of heart A including a wrap 200. Wrap 200 is substantially similar to wrap 11 of FIGS. 1 and 2, except that wrap 200 extends vertically a greater distance than wrap 11. Wrap 200 is not shown with a transventricular splint. It can be appreciated that wrap 200 could be used as restrictive or full cycle device.

Figure 31:
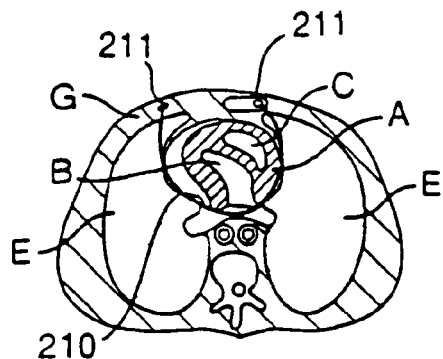
FIG. 31 is a cross sectional view of a patient's torso and heart showing a band splint anchored to the patient's ribs.
Figure 32:
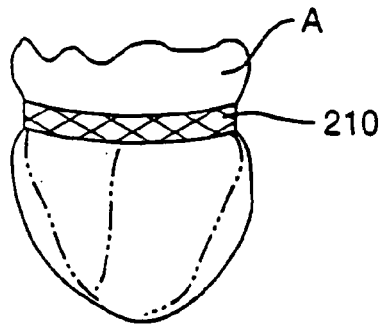
FIG. 32 is a partial vertical view of the heart and band splint of FIG. 31.

FIG. 31 is a horizontal cross section of a human torso including heart A, left ventricle B, right ventricle C, lungs E and ribs G. A wrap 210 is shown partially encircling heart A. Opposite ends of wrap 210 are anchored at 211 to ribs G. At 211, wrap 210 can be anchored to ribs G by bone screw, knot or other means of fastening. It can be appreciated that band splint 210 could be used as a restrictive or full cycle device.

Figure 33:
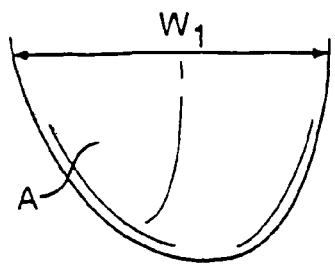
FIG. 33 is a partial vertical view of a failing heart.
Figure 34:
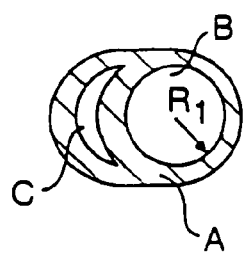
FIG. 34 is a cross sectional view of the heart of FIG. 33.

FIG. 33 is a vertical view of heart A having a $W_1$. FIG. 34 is an idealized horizontal cross sectional view of heart A of FIG. 33. Heart A includes left ventricle B and right ventricle C. Left ventricle B has a radius $R_1$.

Figure 35:
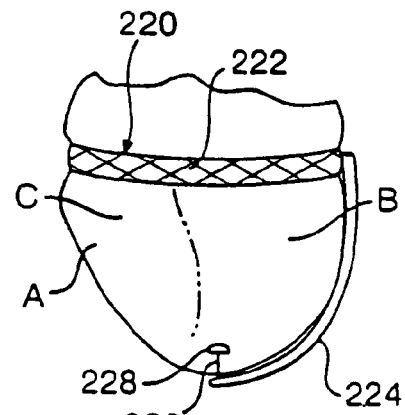
FIG. 35 is a vertical view of the heart for decreasing the horizontal radius of the ventricles and increasing their vertical length.

FIG. 35 is a view of a device 220. Device 220 includes a horizontally encircling band 222 which can be affixed to heart A by sutures, other attachment means or friction fit. Extending from band 222 is a substantially rigid elongate member 224. Member 224 extends to the apex of heart A. Pin 226 extends into left ventricle B of the apex. An anchor or pad 228 is disposed within left ventricle B to anchor the apex of heart A to elongate member 224. Elongate member 224 can be made of sufficient length such that heart A is vertically elongate full cycle, or alternately not at end diastole.

Figure 36:
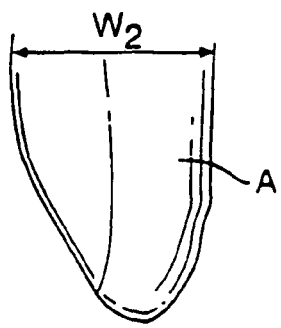
FIG. 36 is an exaggerated vertical view of the heart of FIG. 33 elongated by the device of FIG. 35.
Figure 37:
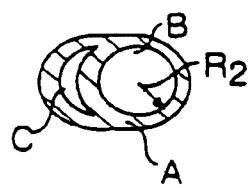
FIG. 37 is a view of the cross section of FIG. 34 showing the decrease in radius of the ventricles.

FIG. 36 is a vertical view of an elongate heart A having a horizontal width $W_2$ less than $W_1$. FIG. 37 is a horizontal cross section of the heart A of FIG. 36 including left ventricle B and right ventricle C. In FIG. 37, the radius $R_2$ of left ventricle B is less than $R_1$ of FIG. 34. Assuming that the hearts of FIGS. 33 and 36 are at the same point in the cardiac cycle, it can be appreciated that the wall stress in heart A is less in FIG. 37 as $R_2$ is shorter R.

If elongate bar 224 is sized such that device 220 does not engage at end diastole, but rather anchor pad 228 first engages during systolic contraction, device 220 can fall into a third class of device neither full cycle nor restrictive. Such a device would reduce wall stress during a portion of systolic contraction including end systole, but not reduce wall stress during end diastole, thus maintaining maximum preload.

Band 222 of device 220 is preferably formed from a web material or other fabric. Band 220 is preferably does not elongate substantially during diastolic filling. Members 224, 226 and 228 are formed from materials which remain substantially rigid under the influences of the forces encountered during the cardiac cycle.

Figure 38:
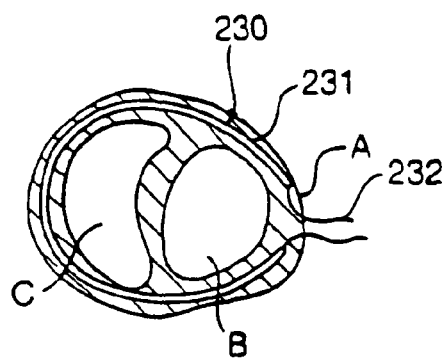
FIG. 38 is a horizontal cross sectional view of the heart showing the left and right ventricles and a splint disposed within the myocardium.

FIG. 38 is a horizontal cross section of heart A including left ventricle B and right ventricle C. Advanced through the myocardium of heart A is a device including a tubular member 231 and thread or line 232 disposed within tubular member 231. In FIG. 38, the free ends of thread 232 are disposed outside of heart A. The free ends of thread 232 could be drawn toward each other to reduce the diameter of device 230 in heart A. After a desired reduction in diameter, the free ends could be tied together.

Tube 231 is preferably highly flexible, yet durable enough to prevent thread 232 from "cheese cutting" through the myocardium of heart A. Tube 231 and line 232 are preferably formed from biocompatible atraumatic materials which do not substantially elongate under the influence of forces encountered during expansion and contraction of heart A. In an alternate embodiment, tube 231 and line 232 could be made from materials which readily elongate under the influence of the forces encountered during the cardiac cycle. It can be appreciated that device 230 could be used as a full cycle device or restrictive device.

Figure 39:
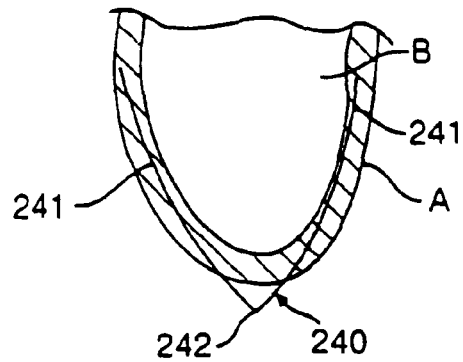
FIG. 39 is a vertical cross section of the left ventricle showing a splint within the myocardium.

FIG. 39 is a vertical cross sectional view of heart A including left ventricle B. A substantially V-shaped or U-shaped member having arms 241 is shown substantially advanced into the myocardium of heart A. Device 240 includes an apex 242 disposed adjacent the apex of heart A. The spacing of arms 241 from each other is preferably such that device 240 can form lobes in horizontal cross sections of left ventricle B.

Device 240 is preferably formed from biocompatible materials which preferably do not deform substantially under the influence of the forces encountered during the cardiac cycle. It can be appreciated that device 240 could be used as a restrictive or full cycle device.

Figure 40:
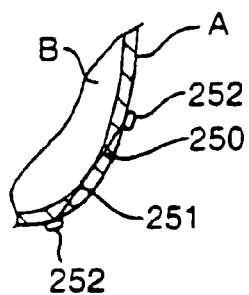
FIG. 40 is a partial cross section of the left ventricle showing a splint extending through a portion of the myocardium.

FIG. 40 is a partial cross section of heart A and left ventricle B. A device 250 extends through a portion of the myocardium of heart A. Device 250 can be configured similarly to splint 12 of FIGS. 1 and 2. Device 250 accordingly includes two tension members 251 and oppositely disposed anchors pad 252. Tension members 251, however, do not extend transventricularly.

Figure 41:
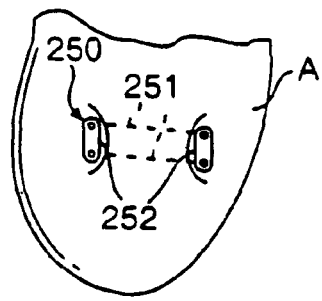
FIG. 41 is a partial vertical view of a heart showing the splint of FIG. 40 extending horizontally through the myocardium.

FIG. 41 is a vertical view of heart A including device 250. Splint 250 can act as a full cycle device or a restrictive device, to shorten a portion of the left ventricle heart wall.

Figure 42:
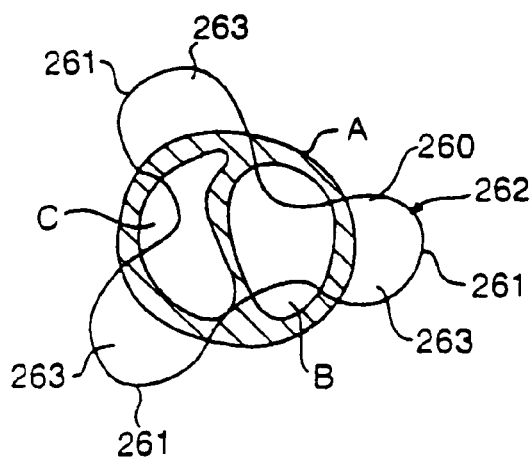
FIG. 42 is a horizontal cross sectional view of the left and right ventricles including reinforcement loops.

FIG. 42 is a horizontal cross sectional view of heart A including left ventricle B and C. A device 260 including a thread or line 261 is disposed transventricularly and transmyocardially through heart A. A portion of line 261 is disposed outside of heart A. Opposite ends of line 261 are connected at 262. Those portions of line 261 outside heart A form loops 263. The size of loops 263 are exaggerated for purposes of illustration. It is assumed that heart A in the process of diastolic filling in FIG. 42, and loops 263 are sufficiently small, eventually heart A will engage loops 263. In such a configuration, device 260 is used as a restrictive device. Loops 263 could be sized, however, such that they engage full cycle.

Line 261 is preferably made from atraumatic biocompatible material. The diameter of line 261 is preferably sufficiently great that cutting of heart A does not occur during diastolic filling.

Figure 43:
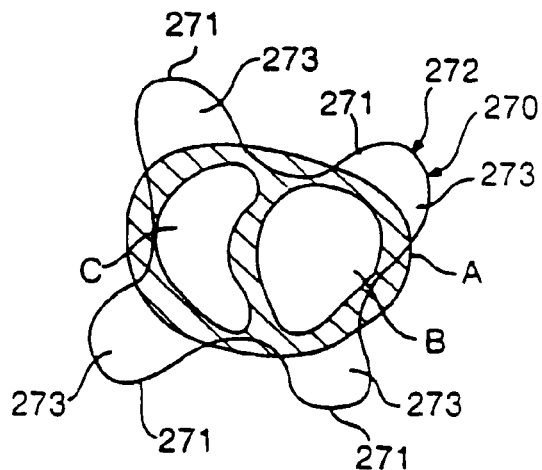
FIG. 43 is an alternate embodiment of the reinforcing loops of FIG. 43.

FIG. 43 is a horizontal cross sectional view of heart A including left ventricle B and right ventricle C and an alternate embodiment 270 of the device of FIG. 42. Device 270 includes a line 271 which does not extend transventricularly but extends through the myocardium of heart A to form four loops 273.

Device 270 can be formed from material similar to that used to form device 260. Additionally, device 270 can be made to function as a restrictive device or full cycle device in a manner similar to that of device 260.

Line 261 and line 267 could be disposed within a tube such as tube 231 of FIG. 38 to avoid cheese cutting of the myocardium. Devices 260 and 270 could extend through the septum or right ventricle to avoid forming lobes in right ventricle C.

Figure 44:
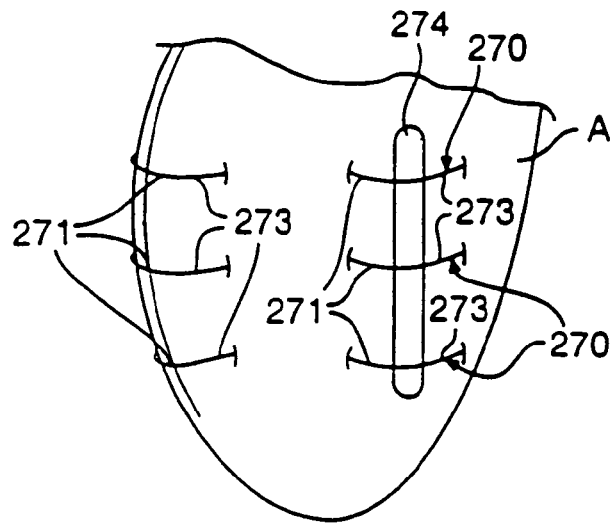
FIG. 44 shows a vertical view of the heart including the reinforcement loops of FIG. 43 and a rigid shape changing member.

FIG. 44 is a vertical view of heart A including three devices 270 disposed at three spaced elevations. An elongate generally rigid bar 274 is disposed through loops 273 to distribute the load on heart A from loops 273 across a larger area than lines 271 can alone.

Figure 45:
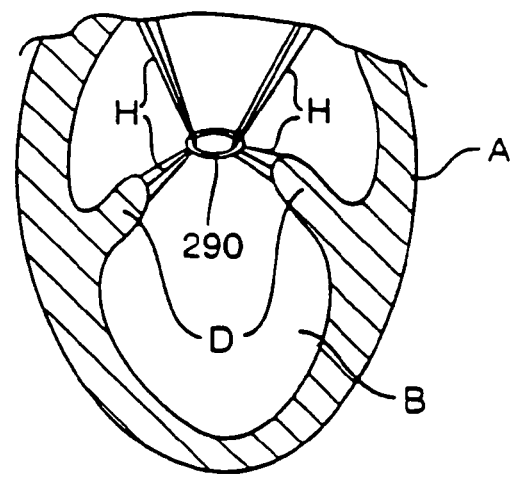
FIG. 45 is a vertical cross sectional view of a heart showing a ring around the chordae.

FIG. 45 is a vertical cross section of heart A showing left ventricle B including papillary muscles D and chordae H. Joining chordae H is a ring 290. Ring 290 is preferably strong and rigid enough to hold chordae H, papillary muscles D and consequently the wall of left ventricle B inward during diastolic expansion. It can be appreciated that loop 290 could be configured to operate as a full cycle or a restrictive device. Preferably loop 229 is formed from an atraumatic biocompatible material.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method for treating a heart having an atrioventricular valve, said method comprising:
   capturing natural chordae of the heart having the atrioventricular valve while the heart is beating by surrounding the natural chordae with a capture device; wherein said capture device is a ring;
   and positioning or configuring the capture device so as to tension at least a portion of the natural chordae to modify movement of the leaflet.

2. The method of claim 1, wherein the capture device is a ring.

3. The method of claim 1, wherein the capture device tensions at least a portion of the natural chordae throughout a cardiac cycle.

4. A method of treating a heart, comprising:
   providing a ring-like structure having an opening;
   positioning the ring-like structure within the left ventricle of the heart;
   capturing the natural chordae of the heart with the ring-like structure such that the natural chordae are positioned within the opening of the ring-like structure; and
   displacing at least one of chordae, papillary muscles, and a wall of the heart via the ring-like structure during a portion of a cardiac cycle.

5. The method of claim 4, wherein the wall of the heart is an external heart wall.

6. The method of claim 4, wherein a portion of the ring-like structure is disposed below a heart valve.

7. The method of claim 4, wherein the displacing step includes displacing each of natural chordae, papillary muscles, and a wall of the heart.

8. The method of claim 4, wherein the wall is a left ventricle wall.

9. The method of claim 4, wherein the displacing step includes displacing natural chordae via the ring-like structure.

10. The method of claim 4, wherein the displacing step includes displacing papillary muscles via the ring-like structure.

11. The method of claim 4, wherein the displacing step includes drawing natural chordae inward with respect to the chamber of the heart.

12. The method of claim 4, wherein the displacing step includes drawing papillary muscles inward with respect to the chamber of the heart.

13. A method of treating a heart, comprising:
capturing a plurality of natural chordae associated with a natural heart valve with a closed ring so that the ring contacts each of the plurality of natural chordae at a position between the natural heart valve and a papillary muscle, wherein capturing the plurality of natural chordae draws each of the plurality of natural chordae toward one another, thereby drawing a wall of a heart chamber inward during a portion of a cardiac cycle.

14. The method of claim 13, wherein the heart chamber is a left ventricle.

15. The method of claim 13, wherein the ring includes an opening and each of the plurality of natural chordae extends through the opening.

16. The method of claim 13, wherein capturing a plurality of natural chordae associated with the natural heart valve with a closed ring includes positioning the ring below a plane of the heart valve and within a left ventricle of the heart.

17. The method of claim 13, wherein the method is performed while the heart is beating.

* * * * *